United States Patent [19]

Grund et al.

[11] Patent Number: 5,554,782
[45] Date of Patent: Sep. 10, 1996

[54] PREPARATION OF DICYANOBENZENES BY AMMONOXIDATION

[75] Inventors: Clemens Grund, Mannheim; Guenther Glas, Meckenheim; Paul Guenthert, Schifferstadt; Helmut Reichelt, Neustadt; Rainer Becker; Arno Lange, both of Bad Duerkheim; Klaus Friedrich, Schifferstadt, all of Germany

[73] Assignee: BASF Aktiengesellschaft, Ludwigshafen, Germany

[21] Appl. No.: 194,461

[22] Filed: Feb. 8, 1994

[30] Foreign Application Priority Data

Feb. 23, 1993 [DE] Germany ............ 43 05 497.8

[51] Int. Cl.$^6$ ................................. C07C 255/51
[52] U.S. Cl. ................................. 558/327; 558/328
[58] Field of Search ....................... 558/327, 328

[56] References Cited

U.S. PATENT DOCUMENTS

| 3,783,142 | 1/1974 | Bakke et al. ............ 558/328 X |
| 3,839,398 | 10/1974 | Leto et al. . |
| 4,137,254 | 1/1979 | Larkin . |
| 4,178,304 | 12/1979 | Litvishkov et al. . |
| 4,814,479 | 3/1989 | Engelbach et al. ............ 558/328 |

FOREIGN PATENT DOCUMENTS

| 0222249 | 5/1987 | European Pat. Off. . |
| 0339553 | 11/1989 | European Pat. Off. . |
| 2125132 | 12/1971 | Germany . |
| 3700710 | 7/1988 | Germany . |
| 1181391 | 2/1970 | United Kingdom . |
| 1323188 | 7/1973 | United Kingdom . |
| 1518413 | 7/1978 | United Kingdom . |

Primary Examiner—Robert W. Ramsuer
Attorney, Agent, or Firm—Oblon, Spivak, McClelland, Maier & Neustadt, P.C.

[57] ABSTRACT

A process for the preparation of dicyanobenzenes of the formula

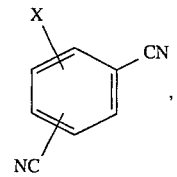

in which x denotes hydroxy, $C_1$–$C_4$ alkoxy, nitro, amino, mono- or di-($C_1$–$C_4$ alkyl)amino, phthalimido or a nitrogenous saturated 5-membered or 6-membered heterocyclic radical, which is attached to the phenyl ring via a nitrogen atom in which a xylene of the formula

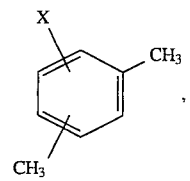

in which
x has the meaning stated above,
is oxidized at a temperature of from 400° to 500° C. with oxygen in the presence of ammonia and a catalyst.

12 Claims, No Drawings

PREPARATION OF DICYANOBENZENES BY AMMONOXIDATION

The present invention relates to a novel process for the preparation of dicyanobenzenes having a further substituent containing oxygen or nitrogen, by oxidation of the corresponding xylenes with oxygen in the presence of ammonia and a catalyst.

U.S. Pat. No. 4,178,304 describes the preparation of o-aminobenonitrile by ammonoxidation of o-toluidine. DE-A 2,125,132 describes such a manufacturing technique starting from o-nitrotoluene. Furthermore, U.S. Pat. No. 4,137,254 describes the conversion of 2,6-dimethylnitrobenzene to 2-amino-3-methylbenzonitrile. Finally, GB-A 1,323,188 describes me preparation of o-nitrotoluene with ammonia in the presence of a dehydrating catalyst.

It is an object of the present invention to provide a novel process for the preparation of dicyanobenzenes by ammonoxidation of the corresponding xylene compounds. The xylenes are required to have an additional functional group, based on an oxygen or nitrogen atom.

We have now found that the preparation of dicyanobenzenes of the formula I

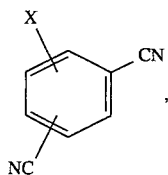

in which x denotes hydroxy, $C_1$–$C_4$ alkoxy, nitro, amino, mono- or di-($C_1$–$C_4$ alkyl)amino, phthalimido or a nitrogenous sate, rated 5-membered or 6-membered heterocyclic radical, which is attached to the phenyl ring via a nitrogen atom is achieved in an advantageous manner, when a xylene of the formula II

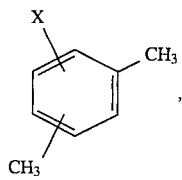

in which x has the meaning stated above, is oxidized at a temperature of from 400° to 500° C. with oxygen in the presence of ammonia and a catalyst.

Suitable radicals x in formulas I and II are, eg, methoxy, ethoxy, propoxy, isopropoxy, butoxy, isobutoxy, sec-butoxy, mono- or di-methylamino, mono- or di-ethylamino, mono- or di-propylamino, mono- or di-isopropylamino, mono- or di-butylamino, mono- or di-isobutylamino, mono- or di-sec-butylamino, pyrrolidinyl, piperidinyl, morpholinyl, piperazinyl, or N-methyl- or N-ethyl-piperazinyl.

A preferred procedure is one in which a xylene of the formula IIa

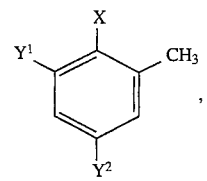

in which one of the two radicals $Y^1$ and $Y^2$ denotes hydrogen and the other denotes methyl and x has the meaning stated above, is oxidized.

A particularly preferred procedure is one in which a xylene of the formula IIb

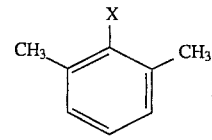

in which x has the meaning stated above, is oxidized.

Yet another particularly preferred procedure is one in which a xylene of the formula II, in which x denotes hydroxy, $C_1$–$C_4$ alkoxy, nitro, or amino, amino being particularly noteworthy, is oxidized.

Dicyanoanilines are mainly produced in the ammonoxidation of nitroxylenes proposed in the present invention.

Suitable catalysts which can be used in the process of the invention are the catalysts commonly used in the ammonoxidation process. This usually involves supported catalysts having a support based on aluminum oxide.

The active catalyst components contained therein are, besides vanadium oxide, other metal oxides, eg, those of tungsten, molybdenum, antimony, bismuth, or titanium. Other components contained in such catalysts, can be, eg, alkali metal oxides, such as lithium oxide, sodium oxide, potassium oxide, rubidium oxide, or cesium oxide, or alkaline-earth metals such as magnesium, calcium, strontium, or barium.

Catalysts of this nature and their preparation are described in, eg, EP-A 222,249 or DE-A 3,700,710.

A particularly suitable catalyst is, for example, one which contains vanadium(V) oxide, antimony(III) oxide, an alkali metal oxide, an alkaline earth metal or an alkaline earth metal compound as well as aluminum oxide, barium being an important example of an alkaline earth metal and barium oxide a significant example of an alkaline earth metal compound.

Particularly interesting, industrially, is a catalyst which contains, in addition to aluminum oxide as support material, from 2 to 10wt % and preferably from 3 to 7 wt % of vanadium(V) oxide, from 1 to 10wt % and preferably from 3 to 7 wt % of antimony(III) oxide, from 0.002 to 2wt % and preferably from 0.1 to 1 wt % of an alkali metal oxide, and from 0.01 to 1 wt % and preferably from 0.1 to 1 wt % of an alkaline earth metal or an alkaline earth metal compound, based, in each case, on the weight of the catalyst. Depending on the method of preparation used, sulfate ions may also be present in the catalyst.

The particle size of the catalyst is usually from 0.06 to 0.4 mm and preferably from 0.1 to 0.3 mm.

The process of the invention is usually carried out under atmospheric pressure and at a temperature of from 400° to 500° C. and preferably from 440° to 490° C. and more preferably from 450° to 480° C., whilst a temperature of ca 470° C. is particularly advantageous.

The oxidizing agent used is oxygen, which is used either undiluted or, if desired, in admixture with an inert gas, eg, nitrogen. The use of undiluted oxygen is preferred. If oxygen is used in admixture with an inert gas, the use of air is preferred.

In our novel process, the reactants xylene of the formula II, oxygen, and ammonia are usually used in a molar ratio of from 1:3:30 to 1:8:80 and preferably from 1:3.5:35 to 1:7:68 and in particular from 1:3.6:37 to 1:6.6:67.5.

The process of the invention is advantageously carried out as follows: a gaseous mixture of the reactants (xylene II, oxygen, and ammonia) is passed through a suitable reactor containing the catalyst and heated at the temperature proposed for the present invention. The residence time of the reaction mixture in the reactor is generally from 0.5 to 15 s and preferably from 1 to 10 s.

A reactor suitable for carrying out our novel process is, for example, a flow tube, eg, in the form of a fluid bed reactor, which can have external heating means, a frit for uniform distribution of the reactants and a candle filter to avoid escape of catalyst.

Advantageous flow tubes usually have a diameter-to-length ratio of from 1:1.5 to 1:25.

The catalyst is generally packed in the reactor in such a manner that the depth of the packing is from 10 to 20% of the height of the reactor. The depth of the fluidized bed is usually from 10 to 30% of the; height of the reactor.

It may in some cases be advantageous to place additional packing material in the reactor together with the catalyst. Suitable packing material comprises, eg, Pall rings or wire spirals.

A special technique to counteract rapid carbonization of the catalyst consists in temporarily stopping the feed of the reactants after a specific period of time (eg 30 min) and passing a mixture of nitrogen and oxygen through the reactor for a period of, say, from 30 to 45 min, at a temperature of from 450° to 490° C. It is particularly favorable to use a gas mixture in which the nitrogen and oxygen are present in a molar ratio of from 30:1 to 30:4.5. Another possibility is to replace the oxygen by air.

On completion of the reaction, the gaseous reaction mixture can be purified by conventional methods, eg, by treatment in scrubbers, in which the condensable components are washed out by suitable solvents, eg, N,N-dimethylformamide,. By subsequently evaporating the solvent followed, if necessary, by washing or recrystallization of the residue there are then obtained the dicyanobenzenes of formula I.

Our novel process can be carried out batchwise or continuously and yields, in a simple manner, the target products showing good values for yield and purity. Another advantage is that using the process of the invention directly produces dinitriles carrying further functional groups. Side reactions, such as the formation of trimeric products, hardly ever occur.

The dicyanobenzenes of formula I are valuable intermediates for the synthesis of dyes or active substances.

The invention is illustrated below with reference to the following examples.

EXAMPLE 1

A fused silica reactor having a length of 1010 mm and an internal diameter of 50 mm and provided with external heating means, a sintered glass frit for uniform distribution of the reaction gases, and a candle filter to prevent escape of catalyst, was packed with 400 mL of a catalyst having a particle size of from 0.1 to 0.33 mm. The depth of the fluidized bed of catalyst was between 20 and 30 cm depending on the gas input rate. The composition of the catalyst was 5.2 wt % of $V_2O_5$, 5.9 wt % of $Sb_2O_3$, 0.37 wt % of $K_2O$, 0.4 wt % of BaO, and 88.13 wt % of $\gamma\text{-}Al_2O_3$.

The reactor was heated to 470° C. 49 g of vaporized 2,6-dimethylaniline were passed therethrough in the form of a gas mixture of 1.9 vol % of 2,6-dimethylaniline, 7.6 vol % of oxygen, and 90.4 vol % of ammonia. The average residence time in the reactor was 1.5 s. The hot reaction gases were passed through a heated bridge to a cascade of scrubbers, in which the condensable components were washed out by N,N-dimethylformamide (DMF). The remaining gas was passed to another scrubber for further washing. The mixture of products was analyzed by gas chromatography, the desired product being additionally determined quantitatively by concentrating the solution, by evaporation, and recrystallizing and weighing the residue.

The total yield of 2,6-dicyanoaniline, based on 2,6-dimethylaniline used, was 20.7 mol %.

EXAMPLES 2 to 4

Example 1 was repeated in each case except that the starting compounds and reaction conditions stated in the following table were used. The corresponding aromatic nitriles were obtained in the yields stated. The average residence time in the reactor was 1.5 s in each case.

| Example No. | Weight of Xylene | Molar Ratio Xylene:$O_2$:$NH_3$ | Yield (mol %) |
| --- | --- | --- | --- |
| 2 | 169 g of 2,3-dimethylaniline | 1:4.6:67.4 | 2.4 |
| 3 | 96 g of 2,4-dimethylaniline | 1:5.1:37.2 | 10.3 |
| 4 | 100 g of 2,6-dimethylaniline | 1:3.8:45.4 | 16.2 |

EXAMPLE 5

Example 1 was repeated except that a total of 66 g of 2,6-dimethylaniline were evaporated. To counteract rapid carbonization of the catalyst, the feed of 2,6-dimethylaniline was interrupted after a period of 30 min, the temperature of the catalyst was lowered by from 10° to 20° C., and a gas mixture of the following composition was passed through the reactor: 9.9 vol % of oxygen and 90.1 vol % of nitrogen. The catalyst was thus regenerated after 45 min. The ammonoxidation of 2,6-dimethylaniline was then continued. The mixture of products was analyzed as described above and the desired product isolated and weighed. This alternating mode of operation was able to produce 2,6-dicyanoaniline in a yield of 26.0 mol %, based on 2,6-dimethylaniline used.

EXAMPLE 6

A fused silica reactor having a length of 600 mm and an internal diameter of 80 mm and provided with external heating means, a sintered glass frit for uniform distribution of the reaction gases, and a candle filter to prevent escape of catalyst, was packed with 400 mL of a catalyst having a particle size of from 0.1 to 0.33 mm. The depth of the fluidized bed of catalyst was between 15 and 20 cm depending on the gas input rate. The composition of the catalyst was 5.5 wt % of $v_2O_5$, 6.6 wt % of $Sb_2O_3$, 0.26 wt % of $K_2O$, and 87.6 wt % of $\gamma\text{-}Al_2O_3$.

The reactor was heated to 470° C. and a mixture of 1.9 vol % of 2,6-dimethylnitrobenzene, 7.6 vol % of oxygen, and 90.4 vol % of ammonia was passed therethrough. The hot reaction gases were passed through a heated bridge to a cascade of scrubbers, in which the condensable components were washed out by DMF. The remaining gas was passed to another scrubber for further washing. The mixture of products was analyzed by gas chromatography, the desired product being additionally determined quantitatively by concentrating the solution, by evaporation, and recrystallizing and weighing the residue.

The total yield of 2,6-dicyanoaniline, based on 2,6-dimethylnitrobenzene used, was 40.3 mol %.

We claim:

1. A process for the preparation of dicyanobenzenes of formula I:

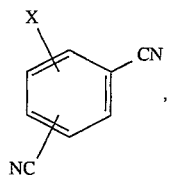
(I)

in which X denotes nitro or amino
wherein a xylene of formula II

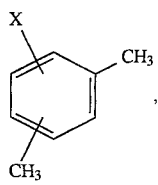
(II)

in which X has the meaning stated above, is oxidized at a temperature of from 400° to 500° C. with oxygen in the presence of ammonia and a catalyst, said catalyst comprising a support and an active catalyst component, said support comprising aluminum oxide, said active catalyst component consisting essentially of 2–10 wt % vanadium (V) oxide, 1–10 wt % antimony (III) oxide, 0.002–2 wt % of an alkali metal oxide and 0.01–1 wt % of an alkaline earth metal or an alkaline earth metal compound.

2. A process as claimed in claim 1, comprising the oxidation of a xylene of the formula IIa

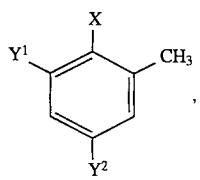
(IIa)

in which one of the two radicals $Y^1$ and $Y^2$ denotes hydrogen and the other denotes methyl and x has the meaning stated above.

3. A process as claimed in claim 1, comprising the oxidation of a xylene of the formula IIb

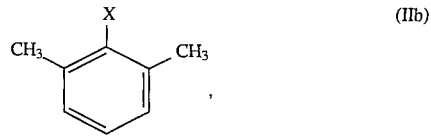
(IIb)

in which x has the meaning stated above.

4. A process as claimed in claimed 1, wherein x denotes amino.

5. A process as claimed in claim 1, wherein the oxidation is carried out at a temperature of from 440° to 490° C.

6. A process as claimed in claim 1, wherein X denotes nitro.

7. A process as claimed in claim 1, said process further comprising the step of isolating said dicyanobenzenes of formula I.

8. A process as claimed in claim 2, said process further comprising the step of isolating said dicyanobenzenes of formula I.

9. A process as claimed in claim 3, said process further comprising the step of isolating said dicyanobenzenes of formula I.

10. A process as claimed in claim 4, said process further comprising the step of isolating said dicyanobenzenes of formula I.

11. A process as claimed in claim 5, said process further comprising the step of isolating said dicyanobenzenes of formula I.

12. A process as claimed in claim 1, wherein said active catalyst component consists essentially of 3–7 wt % vanadium (V) oxide, 0.1 to 1 wt % of an alkali metal oxide and 0.1 to 1 wt % of an alkaline earth metal or an alkaline earth metal compound.

* * * * *